United States Patent

Kusuoka et al.

[11] Patent Number: 5,900,483
[45] Date of Patent: May 4, 1999

[54] PROCESS FOR THE SEPARATION OF PHENYLURACIL COMPOUNDS

[75] Inventors: Yoshiyuki Kusuoka; Yoshihiro Kudo; Norio Tanaka; Jun Satow, all of Funabashi, Japan

[73] Assignee: Nissan Chemical Industries, Ltd., Tokyo, Japan

[21] Appl. No.: 09/138,525

[22] Filed: Aug. 24, 1998

[30] Foreign Application Priority Data

Aug. 29, 1997 [JP] Japan ...................................... 9-233845
Jul. 31, 1998 [JP] Japan ................................... 10-217577

[51] Int. Cl.⁶ ................................................. C07D 239/54
[52] U.S. Cl. ............................................................ 544/312
[58] Field of Search ............................................. 544/312

[56] References Cited

U.S. PATENT DOCUMENTS

| | | | |
|---|---|---|---|
| 5,391,541 | 2/1995 | Konz | 504/243 |
| 5,486,610 | 1/1996 | Strunk et al. | 549/311 |

*Primary Examiner*—John M. Ford
*Attorney, Agent, or Firm*—Oblon, Spivak, McClelland, Maier & Neustadt, P.C.

[57] ABSTRACT

A process for the separation of phenyluracil compounds is provided.

The process according to the present invention comprises treating with a weakly-basic substance a mixture of a halogenophenyluracil compound (I) and a cyanophenyluracil compound (II):

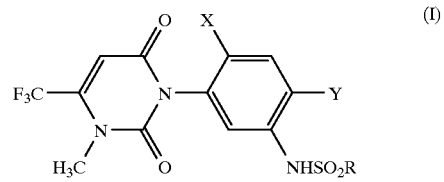

(I)

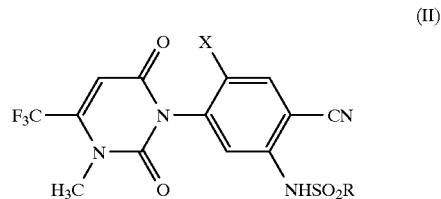

(II)

wherein X is a hydrogen or fluorine atom, Y is a chlorine or bromine atom, and R is an alkyl group containing 1 to 3 carbon atoms, to separate the compounds (I) and (II).

7 Claims, No Drawings

PROCESS FOR THE SEPARATION OF PHENYLURACIL COMPOUNDS

FIELD OF THE INVENTION

The present invention relates to a process for the separation of phenyluracil compounds.

Phenyluracil compounds are useful as biologically active substances in medicines, pesticides and the like and as intermediates thereof. Various analogues thereof have been developed.

PRIOR ARTS

As a process for the preparation of a cyanophenyluracil compound, JP-A-09-048761 describes a process wherein a halogenophenyluracil compound is used as a starting material and a halogen atom on the phenyl group of the halogenophenyluracil compound is replaced with a cyano group. This process has a problem that, when a reaction is not complete, a starting material and a product are hardly separated, since both compounds are similar in structure. Accordingly, a process for efficiently separating the starting material and the product has been sought.

SUMMARY OF THE INVENTION

The present inventors investigated physical properties of the halogenophenyluracil compound and the cyanophenyluracil compound in order to resolve the above problem. As the result, it was confirmed that there is a difference between both compounds with respect to an acidity of sulfoneamide group at 5-position of phenyl nucleus. Then, it was found that by combining this difference with the use of a weakly-basic substance, each compound can be separated in an almost pure form. Further, it was found that the above method can be also applied without any practical problem to a reaction mixture comprising a halogenophenyluracil compound and a cyanophenyluracil compound in any proportion which is obtained by the process as described in JP-A-09-048761.

Accordingly, the present invention comprises a process for the separation of a halogenophenyluracil compound having the formula (I):

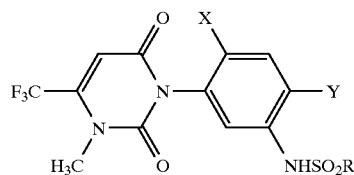

(I)

wherein X is a hydrogen or fluorine atom, Y is a chlorine or bromine atom, and R is an alkyl group containing 1 to 3 carbon atoms, and a cyanophenyluracil compound having the formula (II):

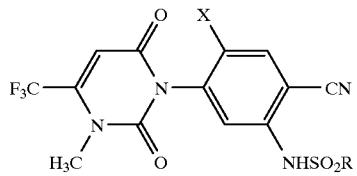

(II)

wherein X and R are as defined above, comprising treating a mixture of the compounds (I) and (II) with a weakly-basic substance.

DETAILED EXPLANATION OF THE INVENTION

According to the present process for the separation of the compounds (I) and (II) in a mixture containing them, only the compound (II) which has an acidity higher than that of the compound (I) may be adsorbed onto the solid weakly-basic substance. Alternatively, only the compound (II) may be converted into its salt by neutralizing with a solution of the weakly-basic substance. The mixture of the compounds (I) and (II) to be treated may be in a solid or molten state. However, the mixture dissolved in a suitable solvent is preferably used in practice.

After the adsorption of the compound (II) or the salt formation of the compound (II), the compounds (I) and (II) are separated each other. For this separation, a dissolution in a suitable solvent or an extraction with a suitable solvent is preferably conducted.

A practical process for the separation comprising adsorbing onto the solid weakly-basic substance is conducted as follows. A solution of the mixture of the compounds (I) and (II) is contacted with the solid weakly-basic substance so that only the compound (II) is selectively adsorbed onto the solid weakly-basic substance. After the compound (I) is selectively taken out as its solution, the compound (II) adsorbed on the solid weakly-basic substance is treated with a solution comprising a substance which has a basicity higher than that of the solid weakly-basic substance so that the compound (II) is desorbed from the solid weakly-basic substance.

For the adsorption onto the solid weakly-basic substance, any suitable method may be selected from known methods including a method of batchwise mixing a slurry and a method of continuously adsorbing and desorbing in a column or a fixed bed in which the solid weakly-basic substance is filled.

A process for the separation comprising forming the salt of the compound (II) with the solution of the weakly-basic substance is conducted as follows. The solution of the mixture of the compounds (I) and (II) is mixed with the solution of the weakly-basic substance so that only the compound (II) is converted into its salt. Then, when the mixture is separated into layers, either layer is taken out. When the mixture is in the form of an uniform solution or slurry, it may be filtered or concentrated followed by adding a suitable solvent to form a solution in which either the free compound (I) or the salt of the compound (II) is selectively dissolved. Then, the solution is separated.

Examples of the weakly-basic substance usable in the present invention include sodium, potassium and lithium hydrogencarbonates; ammonium carbonate; and aluminum, zinc, cerium, tin and titanium oxides. The weakly-basic substance may be used in the form of solid or solution.

As the solid weakly-basic substance, aluminum, zinc, cerium, tin and titanium oxides are preferable. Aluminum oxide (alumina) is particularly preferable in respect of its usability.

As the solution of the weakly-basic substance, an aqueous solution is preferable in practice. Examples of the weakly-basic substance contained in the solution include sodium, potassium and lithium hydrogencarbonates and ammonium carbonate. Sodium and potassium hydrogencarbonates are preferable.

An amount of the weakly-basic substance to be used is such that the compound (II) to be separated is necessarily adsorbed or converted into its salt. In case of the adsorption, usually the solid weakly-basic substance should be used in excess of a theoretical amount, considering factors such as a specific surface area of the solid and an adsorption equilibrium. On the other hand, in case of the salt formation, the use of the weakly-basic substance in a theoretical amount is enough since the compound (II) is very selectively converted into its salt based on the difference in acidity between the compounds (I) and (II). In practice, the weakly-basic substance can be used in an amount ranging from the theoretical amount to 100 times thereof, preferably from the theoretical amount to 20 times thereof.

In the preparation of the solution comprising the compounds (I) and (II) and the separation thereof, various solvents may be used. Non-limiting examples of the generally used solvents according to the present invention which may be also industrially used include alcohols such as methanol, ethanol, isopropanol, n-propanol, 1-butanol, isobutanol, 1-pentanol, 1-hexanol cyclohexanol, benzylalcohol, methoxyethanol, ethoxyethanol and isopropoxyethanol; esters such as methyl, ethyl, butyl and isoamyl acetates and methyl and ethyl propionates; ketones such as acetone, methyl ethyl ketone, 3-pentanone, methyl isobutyl ketone, cyclopentanone and cyclohexanone; aromatic solvents such as benzene, toluene, xylene, mesitylene, chlorobenzene, o-dichlorobenzene and anisole; aliphatic hydrocarbons such as pentane, hexane, cyclohexane, heptane, methylcylohexane and octane; halogenated aliphatic hydrocarbons such as dichloromethane, chloroform, carbon tetrachloride, 1,2-dichloroethane and tetrachloroethylene; ethers such as tert-amyl methyl ether, tert-butyl ethyl ether, dipropyl ether, dibutyl ether, diisobutyl ether, ethoxy propoxy ethane, 1,1-dimethoxyethane, 1,2-dimethoxyethane, diethylene glycol dimethyl ether, diethylene glycol dibutyl ether, tetrahydrofuran and 1,4-dioxane; nitriles such as acetonitrile, propionitrile, butyronitrile and isobutyronitrile; formamide; N-methylformamide; N,N-dimethylformamide; N,N-dimethylacetamide; N-methylpyrrolidone; N,N,N,N-tetramethylurea; N,N,N,N-tetrabutylurea; 1,3-dimethylimidazolidinone; dimethyl sulfoxide; sulfolane; and water.

The solvent may be selected depending on criteria such as solubilities of the compounds (I) and (II) and an easiness of separation and recovery. If necessary, a combination of two or more solvents may be used. When such a combination is used, a combination of the solvents which are nearly insoluble each other may be selected. Or, alternatively a combination of the solvents which are soluble each other and can be subsequently separated and recovered based on the difference in boiling point thereof and the like may be selected. Thus, a separation process excellent in economy and productivity can be constituted. The use of a combination of water with an organic solvent slightly soluble or insoluble in water is particularly preferable.

An amount of the solvent used for the separation is selected considering productivity, workability and solubilities of the compounds (I) and (II) to be separated. Generally, it is 1 to 100 parts by weight, preferably 1 to 50 parts by weight with respect to the mixture of the compounds (I) and (II).

A temperature during the separation is not particularly limited. Heating is also possible when changes of any factors such as the solubilities of the compounds (I) and (II), a salt formation rate and an adsorption/desorption rate is required. Generally, the temperature is preferably in the range from room temperature to a boiling point of the solvent used. In practice, the temperature ranging from room temperature to 100° C. is preferable.

Further, in case of the crude compound (II) in which the compound (I) is not contained, the compound (II) may be separated and purified by treating the crude compound (II) with the weakly-basic substance.

EXAMPLES

The present invention is illustrated in the following examples which are not intended to limit the invention.

Example 1

Separation of 1-methyl-3-(4-chloro-5-ethanesulfonylamino-2-fluorophenyl)-6-trifluoromethyl-2,4-(1H,3H)pyrimidinedione and 1-methyl-3-(4-cyano-5-ethanesulfonylamino-2-fluorophenyl)-6-trifluoromethyl-2,4-(1H,3H) pyrimidinedione To a mixture of 1-methyl-3-(4-chloro-5-ethanesulfonylamino-2-fluorophenyl)-6-trifluoromethyl-2,4-(1H,3H)pyrimidinedione (4.30 g, 10 mmol) and 1-methyl-3-(4-cyano-5-ethanesulfonylamino-2-fluorophenyl)-6-trifluoromethyl-2,4-(1H,3H)pyrimidinedione (4.20 g, 10 mmol), a saturated aqueous sodium hydrogencarbonate solution (150 ml) and 1,2-dichloroethane (200 ml) were added. The whole was warmed to 50° C., stirred for 10 minutes, and then allowed to stand for 5 minutes. After an organic layer was separated, an additional 1,2-dichloroethane (50 ml) was added to an aqueous layer to extract soluble matters. The resulting organic layers were concentrated under reduced pressure to obtain crystals. An analysis of the crystals showed that 4.26 g (recovery: 99%) of 1-methyl-3-(4-chloro-5-ethanesulfonylamino-2-fluorophenyl)-6-trifluoromethyl-2,4-(1H,3H) pyrimidinedione was contained therein. While, the aqueous layers were acidified with 5N hydrochloric acid to precipitate crystals. The crystals were filtered off, washed with water (20 ml×4), and then dried under reduced pressure. The crystals contained 4.07 g (recovery: 97%) of 1-methyl-3-(4-cyano-5-ethanesulfonylamino-2-fluorophenyl)-6-trifluoromethyl-2,4-(1H,3H)pyrimidinedione with a purity of 99.7%.

Example 2

Separation of 1-methyl-3-(4-chloro-5-ethanesulfonylamino-2-fluorophenyl)-6-trifluoromethyl-2,4-(1H,3H)pyrimidinedione and 1-methyl-3-(4-cyano-5-ethanesulfonylamino-2-fluorophenyl)-6-trifluoromethyl-2,4-(1H,3H) pyrimidinedione To a solution of 1-methyl-3-(4-chloro-5-ethanesulfonylamino-2-fluorophenyl)-6-trifluoromethyl-2,4-(1H,3H)pyrimidinedione (2.15 g, 5 mmol) and 1-methyl-3-(4-cyano-5-ethanesulfonylamino-2-fluorophenyl)-6- trifluoromethyl-2,4-(1H,3H)pyrimidinedione (2.10 g, 5 mmol) in N-methylpyrrolidone (150 ml), a saturated aqueous potassium hydrogencarbonate solution (50 ml) was added. After stirring at 50° C. for 1 hour, the solvent was evaporated to complete dryness at the temperature of 70° C. or less under reduced pressure. After adding acetonitrile (100 ml) to the thus-produced solid mixture, the whole was stirred at room temperature for 30 minutes and filtered. A solid remained was further washed with acetonitrile (30 ml×2). An analysis of the resulting acetonitrile solutions after the concentration to dryness under reduced pressure showed that 2.11 g (recovery: 98%) of 1-methyl-3-(4-chloro-5-ethanesulfonylamino- 2-fluorophenyl)-6-trifluoromethyl-2,4-(1H,3H)pyrimidinedione was contained therein. While, an analysis of the solid remained after the filtration showed that 2.27 g (recovery: 99%) of the potassium salt of 1-methyl-3-(4-cyano-5-ethanesulfonylamino-2-fluorophenyl)-6-trifluoromethyl-2,4-(1H,3H) pyrimidinedione with a purity of 99.2% was contained therein.

Example 3

Separation of 1-methyl-3-(4-chloro-5-ethanesulfonylamino-2-fluorophenyl)-6-trifluoromethyl-2,4-(1H,3H)pyrimidinedione and 1-methyl-3-(4-cyano-5-ethanesulfonylamino-2-fluorophenyl)-6-trifluoromethyl-2,4-(1H,3H) pyrimidinedione To a solution of 1-methyl-3-(4-chloro-5-ethanesulfonylamino-2-fluorophenyl)-6-trifluoromethyl-2,4-(1H,3H)pyrimidinedione (2.15 g, 5 mmol) and 1-methyl-3-(4-cyano-5-ethanesulfonylamino-2-fluorophenyl)-6-trifluoromethyl-2,4-(1H,3H)pyrimidinedione (2.10 g, 5 mmol) in N-methylpyrrolidone (150 ml), a saturated aqueous sodium hydrogencarbonate solution (100 ml) was added. After stirring at 50° C. for 1 hour, the solvent was evaporated to complete dryness at the temperature of 70° C. or less under reduced pressure. After adding water (100 ml) to the thus-produced solid mixture, the whole was stirred at room temperature for 30 minutes and filtered. A solid remained was further washed with water (50 ml×2). The resulting aqueous solutions were acidified with 5N hydrochloric acid to precipitate crystals. The crystals were filtered off, washed with water (20 ml×4) and then dried under reduced pressure. The crystals contained 2.04 g (recovery: 97%) of 1-methyl-3-(4-cyano-5-ethanesulfonylamino-2-fluorophenyl)-6-trifluoromethyl-2,4-(1H,3H) pyrimidinedione with a purity of 99.6%. While, an analysis of the solid remained showed that 2.11 g (recovery: 98%) of 1-methyl-3-(4-chloro-5-ethanesulfonylamino-2-fluorophenyl)-6-trifluoromethyl-2,4-(1H,3H) pyrimidinedione with a purity of 99.2% was contained therein.

Example 4

Separation of 1-methyl-3-(4-chloro-5-ethanesulfonylamino-2-fluorophenyl)-6-trifluoromethyl-2,4-(1H,3H)pyrimidinedione and 1-methyl-3-(4-cyano-5-ethanesulfonylamino-2-fluorophenyl)-6-trifluoromethyl-2,4-(1H,3H) pyrimidinedione A solution of 1-methyl-3-(4-chloro-5-ethanesulfonylamino-2-fluorophenyl)-6-trifluoromethyl-2,4-(1H,3H)pyrimidinedione (2.15 g, 5 mmol) and 1-methyl-3-(4-cyano-5-ethanesulfonylamino-2-fluorophenyl)-6-trifluoromethyl-2,4-(1H,3H)pyrimidinedione (2.10 g, 5 mmol) in acetonitrile (100 ml) was charged in a column filled with 100 g of a basic alumina (aluminum oxide 60PF, ex Merck & Co. Inc.) followed by eluting with acetonitrile (300 ml). After the resulting acetonitrile solution was concentrated under reduced pressure, 2.06 g (recovery: 96%) of 1-methyl-3-(4-chloro-5-ethanesulfonylamino-2-fluorophenyl)-6-trifluoromethyl-2,4-(1H,3H) pyrimidinedione was obtained. Then, the column was eluted with 200 ml of a mixed solution of acetonitrile/water/triethylamine (85/10/5 by volume). The resulting solution was concentrated and then acidified with 5N hydrochloric acid to precipitate crystals. The crystals were filtered off, washed with water (10 ml×5), and then dried under reduced pressure. Thus, 1.95 g (recovery: 93%) of 1-methyl-3-(4-cyano-5-ethanesulfonylamino-2-fluorophenyl)-6-trifluoromethyl-2,4-(1H,3H)pyrimidinedione was obtained with a purity of 99.3%.

Example 5

Separation of 1-methyl-3-(4-bromo-5-ethanesulfonylamino-2-fluorophenyl)-6-trifluoromethyl-2,4-(1H,3H)pyrimidinedione and 1-methyl-3-(4-cyano-5-ethanesulfonylamino-2-fluorophenyl)-6-trifluoromethyl-2,4-(1H,3H) pyrimidinedione To a mixture of 1-methyl-3-(4-bromo-5-ethanesulfonylamino- 2-fluorophenyl)-6-trifluoromethyl-2, 4-(1H,3H)pyrimidinedione (4.74 g, 10 mmol) and 1-methyl-3-(4-cyano-5-ethanesulfonylamino-2-fluorophenyl)-6-trifluoromethyl-2,4-(1H,3H)pyrimidinedione (4.20 g, 10 mmol), a saturated aqueous sodium hydrogencarbonate solution (150 ml) and chloroform (200 ml) were added. The whole was warmed to 50° C., stirred for 10 minutes, and then allowed to stand for 5 minutes. After an organic layer was separated, an aqueous layer was extracted with an additional chloroform (50 ml). The resulting organic layers were concentrated under reduced pressure to obtain crystals. An analysis of the crystals showed that 4.72 g (recovery: 99.5%) of 1-methyl-3-(4-bromo-5-ethanesulfonylamino-2-fluorophenyl)-6-trifluoromethyl-2,4-(1H,3H) pyrimidinedione was contained therein. While, the aqueous layers were acidified with 5N hydrochloric acid to precipitate crystals. The crystals were filtered off, washed with water (20 ml×3), and then dried under reduced pressure. The crystals contained 4.14 g (recovery: 98.5%) of 1-methyl-3-(4-cyano-5-ethanesulfonylamino-2-fluorophenyl)-6-trifluoromethyl-2,4-(1H,3H)pyrimidinedione with a purity of 99.7%.

Example 6

Separation of 1-methyl-3-(4-chloro-2-fluoro-5-methanesulfonylaminophenyl)-6-trifluoromethyl-2, 4-(1H,3H)pyrimidinedione and 1-methyl-3-(4-cyano-2-fluoro-5-methanesulfonylaminophenyl)-6-trifluoromethyl-2,4-(1H,3H)pyrimidinedione To a mixture of 1-methyl-3-(4-chloro-2-fluoro-5-methanesulfonylaminophenyl)-6-trifluoromethyl-2,4-(1H, 3H)pyrimidinedione (4.16 g, 10 mmol) and 1-methyl-3-(4-cyano-2-fluoro-5-methanesulfonylaminophenyl)-6-trifluoromethyl-2,4-(1H,3H)pyrimidinedione (4.06 g, 10 mmol), a saturated aqueous sodium hydrogencarbonate solution (150 ml) and chloroform (200 ml) were added. The whole was warmed to 50° C., stirred for 10 minutes, and then allowed to stand for 5 minutes. After an organic layer was separated, an aqueous layer was extracted with an additional chloroform (50 ml). The resulting organic layers were concentrated under reduced pressure to obtain crystals. An analysis of the crystals showed that 4.10 g (recovery: 98.5%) of 1-methyl-3-(4-chloro-2-fluoro-5-methanesulfonylaminophenyl)-6-trifluoromethyl-2,4-(1H, 3H)pyrimidinedione was contained therein. While, the aqueous layers were acidified with 5N hydrochloric acid to precipitate crystals. The crystals were filtered off, washed with water (20 ml×3), and then dried under reduced pressure. The crystals contained 3.94 g (recovery: 97%) of 1-methyl-3-(4-cyano-2-fluoro-5-methanesulfonylaminophenyl)-6-trifluoromethyl-2,4-(1H, 3H)pyrimidinedione with a purity of 99.0%.

Example 7

Separation of 1-methyl-3-(4-bromo-5-ethanesulfonylamino-2-fluorophenyl)-6-trifluoromethyl-2,4-(1H,3H)pyrimidinedione and 1-methyl-3-(4-cyano-5-ethanesulfonylamino-2-fluorophenyl)-6-trifluoromethyl-2,4-(1H,3H) pyrimidinedione from a reaction liquid A solution of 1-methyl-3-(4-bromo-5-ethanesulfonylamino-2-fluorophenyl)-6-trifluoromethyl-2, 4-(1H,3H)pyrimidinedione (4.74 g, 10 mmol) and cuprous cyanide (1.03 g, 11.5 mmol) in N,N-dimethylformamide (30 ml) was stirred at a reflux temperature in a nitrogen gas atmosphere for 4 hours to react. After the reaction was complete, the reaction liquid was cooled, to which a mixed solution of ferric chloride (4.5 g), water (6 ml) and 35% hydrochloric acid (1.5 ml) was gradually added. After stirring at room temperature for 10 minutes, water (100 ml) was added and then an extraction with chloroform (100 ml×2) was conducted. An internal standard quantitative analysis according to high performance liquid chromatography of the resulting chloroform layers showed that 0.43 g (residual content of the starting material: 9%) of the starting material, 1-methyl-3-(4-bromo-5-ethanesulfonylamino-2-fluorophenyl)-6-trifluoromethyl-2,4-(1H,3H) pyrimidinedione and 3.70 g (yield: 88%) of the product, 1-methyl-3-(4-cyano-5-ethanesulfonylamino-2-fluorophenyl)-6-trifluoromethyl-2,4-(1H,3H) pyrimidinedione were contained therein.

A saturated aqueous sodium hydrogencarbonate solution (150 ml) was added to the organic layer. The whole was warmed to 50° C., stirred for 10 minutes, and then allowed to stand for 5 minutes. After an organic layer was separated, an aqueous layer was extracted with an additional chloroform (50 ml). The resulting organic layers were concentrated under reduced pressure to obtain crystals. An analysis of the crystals showed that 0.42 g (recovery: 98%) of the starting material, 1-methyl-3-(4-bromo-5-ethanesulfonylamino-2-fluorophenyl)-6-trifluoromethyl-2,4-(1H,3H) pyrimidinedione was contained therein. While, the remaining aqueous layers were acidified with 10N hydrochloric acid to precipitate crystals. The crystals were filtered off, washed with water (20 ml×3), and then dried under reduced pressure. The crystals contained 3.66 g (recovery: 99%) of the objective compound, 1-methyl-3-(4-cyano-5-ethanesulfonylamino-2-fluorophenyl)-6-trifluoromethyl-2, 4-(1H,3H)pyrimidinedione with a purity of 99.7%.

Example 8

Separation of 1-methyl-3-(4-chloro-2-fluoro-5-methanesulfonylaminophenyl)-6-trifluoromethyl-2, 4-(1H,3H)pyrimidinedione and 1-methyl-3-(4-cyano-2-fluoro-5-methanesulfonylaminophenyl)-6-trifluoromethyl-2,4-(1H,3H)pyrimidinedione from a reaction liquid A solution of 1-methyl-3-(4-chloro-2-fluoro-5-methanesulfonylaminophenyl)-6-trifluoromethyl-2,4-(1H, 3H)pyrimidinedione (4.16 g, 10 mmol) and cuprous cyanide (1.03 g, 11.5 mmol) in N,N-dimethylformamide (30 ml) was stirred at a reflux temperature in a nitrogen gas atmosphere for 2 hours to react. After the reaction was complete, the reaction liquid was cooled to the temperature of 30° C., to which a mixed solution of ferric chloride (4.5 g), water (6 ml) and 35% hydrochloric acid (1.5 ml) was gradually added. The whole was stirred at the same temperature for 10 minutes. Then, water (100 ml) was added and an extraction with chloroform (100 ml×2) was conducted. An internal standard quantitative analysis according to high performance liquid chromatography of the resulting chloroform layers showed that 1.29 g (residual content of the starting material: 31%) of the starting material, 1-methyl-3-(4-chloro-2-fluoro-5-methanesulfonylaminophenyl)-6-trifluoromethyl-2,4-(1H,3H)pyrimidinedione and 2.68 g (yield: 66%) of the product, 1-methyl-3-(4-cyano-2-fluoro-5-methanesulfonylaminophenyl)-6-trifluoromethyl-2,4-(1H,3H)pyrimidinedione were contained therein.

A saturated aqueous sodium hydrogencarbonate solution (150 ml) was added to the organic layer. The whole was warmed to 50° C., stirred for 10 minutes, and then allowed to stand for 5 minutes. After an organic layer was separated, an aqueous layer was extracted with an additional chloroform (50 ml). The resulting organic layers were concentrated under reduced pressure to obtain crystals. An analysis of the crystals showed that 1.28 g (recovery: 99%) of the starting material, 1-methyl-3-(4-chloro-2-fluoro-5-methanesulfonylaminophenyl)-6-trifluoromethyl-2,4-(1H, 3H)pyrimidinedione was contained therein. While, the remaining aqueous layers were acidified with 5N hydrochloric acid to precipitate crystals. The crystals were filtered off, washed with water (20 ml×3), and then dried under reduced pressure. The crystals contained 2.63 g (recovery: 98%) of the objective compound, 1-methyl-3-(4-cyano-2-fluoro-5-methanesulfonylaminophenyl)-6-trifluoromethyl-2,4-(1H, 3H)pyrimidinedione with a purity of 99.4%.

Example 9

Separation of 1-methyl-3-(4-bromo-5-ethanesulfonylamino-2-fluorophenyl)-6-trifluoromethyl-2,4-(1H,3H)pyrimidinedione and 1-methyl-3-(4-cyano-5-ethanesulfonylamino-2-fluorophenyl)-6-trifluoromethyl-2,4-(1H,3H) pyrimidinedione A mixture of 1-methyl-3-(4-bromo-5-ethanesulfonylamino-2-fluorophenyl)-6-trifluoromethyl-2, 4-(1H,3H)pyrimidinedione (4.74 g, 10 mmol) and 1-methyl-3-(4-cyano-5-ethanesulfonylamino-2-fluorophenyl)-6-trifluoromethyl-2,4-(1H,3H)pyrimidinedione (4.20 g, 10 mmol) was dissolved in butyl acetate (100 ml). A 5% aqueous potassium hydrogencarbonate solution (50 ml) was added. The whole was warmed to 30° C., stirred for 10 minutes, and then allowed to stand for 5 minutes. The extraction was repeated until an evolution of $CO_2$ gas was not observed, thereby aqueous layers were separated. The thus-obtained aqueous solution was acidified to pH<3 with 10% hydrochloric acid at the room temperature to precipitate crystals. The crystals were filtered off, washed with water (20 ml×3), and then dried under reduced pressure. The crystals contained 4.07 g (recovery: 97%) of 1-methyl-3-(4-cyano-5-ethanesulfonylamino-2-fluorophenyl)-6-trifluoromethyl-2,4-(1H,3H)pyrimidinedione with a purity of 99.7%. While, the remaining butyl acetate solution was washed with water (100 ml) and dried. Thus, 4.72 g (recovery: 99.5%) of 1-methyl-3-(4-bromo-5- ethanesulfonylamino-2-fluorophenyl)-6-trifluoromethyl-2,4-(1H,3H)pyrimidinedione was obtained.

Example 10

Separation of 1-methyl-3-(4-bromo-5-ethanesulfonylamino-2-fluorophenyl)-6-trifluoromethyl-2,4-(1H,3H)pyrimidinedione and 1-methyl-3-(4-cyano-5-ethanesulfonylamino-2-fluorophenyl)-6-trifluoromethyl-2,4-(1H,3H) pyrimidinedione from a reaction liquid To a solution of 1-methyl-3-(4-bromo-5-ethanesulfonylamino-2-fluorophenyl)-6-trifluoromethyl-2,4-(1H,3H)pyrimidinedione (4.74 g, 10 mmol) and cuprous cyanide (1.08 g, 12 mmol) in N,N-dimethylformamide (30 ml), toluene (30 ml) was added. After the solution was sufficiently subjected to azeotropic dehydration at 80° C. under reduced pressure, toluene was completely evaporated. Then, the whole was stirred at reflux temperature under normal pressure in an argon atmosphere for 4 hours to react. After the reaction was complete, the reaction liquid was cooled, to which 10% hydrochloric acid (10 ml) was gradually added followed by stirring at room temperature. After adding water (50 ml) and butyl acetate (100 ml), the whole was stirred for 10 minutes. Insoluble solids were filtered off. After an aqueous layer was taken out of the resulting solution, a 5% aqueous potassium hydrogencarbonate solution (50 ml) was added to the aqueous layer, which was warmed to 30° C., stirred for 10 minutes, and then allowed to stand for 5 minutes. An extraction was repeated until an evolution of $CO_2$ gas was not observed, thereby aqueous layers were separated. The thus-obtained aqueous solution was acidified to pH<3 with 10% hydrochloric acid at room temperature to precipitate crystals. The crystals were filtered off, washed with water (20 ml×3), and then dried under reduced pressure. The crystals contained 2.86 g (yield: 68%) of 1-methyl-3-(4-cyano-5-ethanesulfonylamino-2-fluorophenyl)-6-trifluoromethyl-2,4-(1H,3H) pyrimidinedione with a purity of 99.1%. The remaining organic layers were washed with water (100 ml) and then concentrated under reduced pressure to obtain crystals. An analysis of the crystals showed that 1.42 g (recovery: 30%) of the starting material, 1-methyl-3-(4-bromo-5-ethanesulfonylamino-2-fluorophenyl)-6-trifluoromethyl-2,4-(1H,3H)pyrimidinedione was contained therein.

We claim:

1. A process for the separation of a halogenophenyluracil compound having the formula (I):

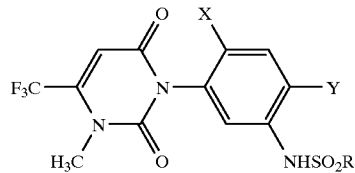

(I)

wherein X is a hydrogen or fluorine atom, Y is a chlorine or bromine atom, and R is an alkyl group containing 1 to 3 carbon atoms, and a cyanophenyluracil compound having the formula (II):

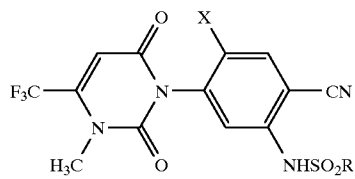

(II)

wherein X and R are as defined above, comprising treating a mixture of the compounds (I) and (II) with a weakly-basic substance.

2. A process as claimed in claim 1, wherein the compound (II) is converted into its salt with the weakly-basic substance.

3. A process as claimed in claim 1, wherein the compound (II) is adsorbed onto the weakly-basic substance.

4. A process as claimed in claim 1, wherein the weakly-basic substance is in the form of solution or solid.

5. A process as claimed in claim 4, wherein the solution is an aqueous solution of sodium or potassium hydrogencarbonate.

6. A process as claimed in claim 4, wherein the solid is basic alumina.

7. A process as claimed in claim 1, wherein the mixture of the compounds (I) and (II) is a mixture which results from the reaction for preparing the compound (II) comprising reacting the compound (I) with cuprous, sodium or potassium cyanide and contains the compound (I) unreacted and the thus-prepared compound (II).

* * * * *